United States Patent [19]  
Bizot et al.

[11] 3,935,092  
[45] Jan. 27, 1976

[54] PURIFICATION OF A CHLORIDE SOLUTION
[75] Inventors: Jean Bizot, Essonne; André Sausse, Hauts-de-Seine, both of France
[73] Assignee: Rhone-Poulenc-Textile, Paris, France
[22] Filed: Mar. 21, 1974
[21] Appl. No.: 453,532

Related U.S. Application Data
[62] Division of Ser. No. 315,196, Dec. 14, 1972.

[30] Foreign Application Priority Data
Dec. 14, 1971  France .............................. 71.44868

[52] U.S. Cl. ................ 204/234; 204/130; 204/131; 204/149; 204/152; 210/321
[51] Int. Cl.² ..................................... C25D 21/00
[58] Field of Search .......... 204/149, 98, 130, 180 P, 204/128, 234, 235, 228; 210/22, 62, 321; 209/301–302

[56] References Cited  
UNITED STATES PATENTS
3,076,754  2/1963  Evans ................................. 204/237
3,149,060  9/1964  Dobry et al. ..................... 204/180 R
3,390,065  6/1968  Cooper ............................. 204/98 X
3,691,068  9/1972  Cross ..................................... 210/22
3,829,370  8/1974  Bourat ............................. 204/180 P OTHER PUBLICATIONS
Kruse et al., Alien Property Custodian Ser. No. 173,206; June 22, 1943.
Turtle, "Automated Chlorine Residual Control," Jrnl. AWWA, June 1969, pp. 293–296.

Primary Examiner—John H. Mack  
Assistant Examiner—A. C. Prescott  
Attorney, Agent, or Firm—Cushman, Darby & Cushman

[57] ABSTRACT

A process and apparatus for purification of a sodium chloride solution dialysis liquid in which the liquid is subjected to an electrolysis.

2 Claims, 1 Drawing Figure

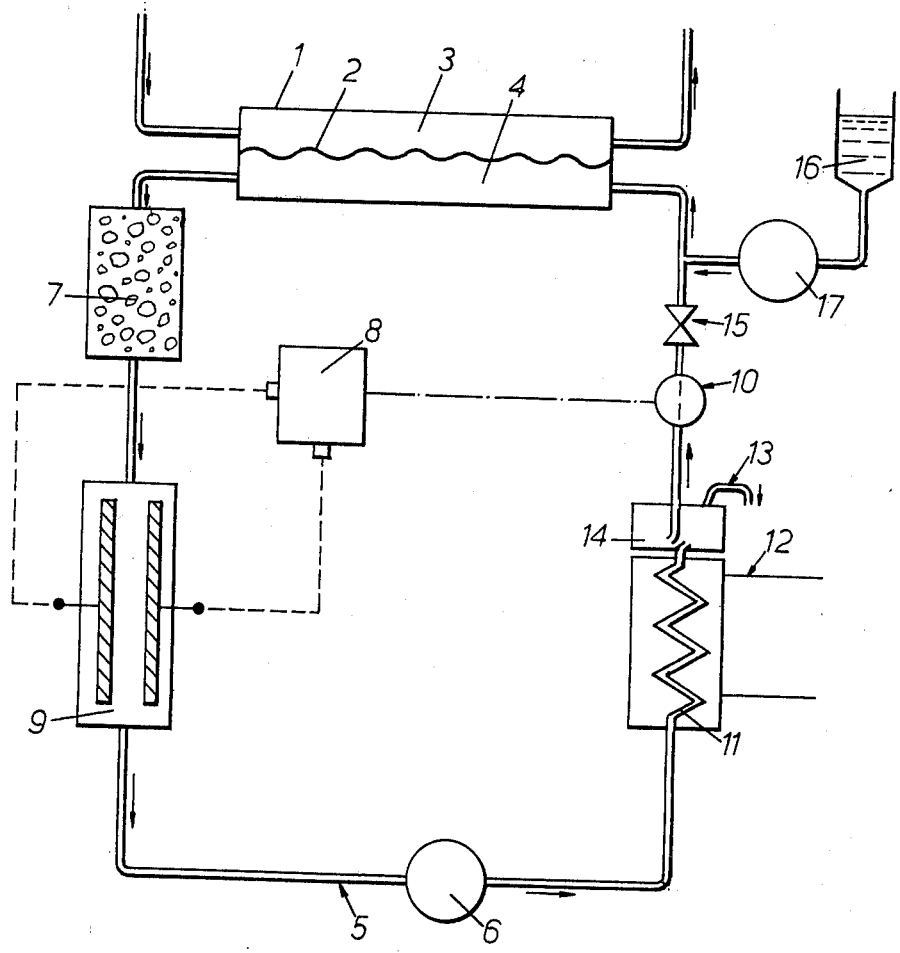

PURIFICATION OF A CHLORIDE SOLUTION

This is a division of application Ser. No. 315,196 filed Dec. 14, 1972.

The present invention relates to the purification of a solution of sodium chloride containing oxidisable waste matter which originated from blood and has passed through a membrane, for example, the purification of blood ultrafiltrate, or the purification and regeneration of a blood dialysis liquid.

Amongst these various applications, the regeneration of a blood dialysis liquid has formed the subject of many investigations. In effect, the treatment of renal insufficiencies by haemodialysis sessions requires, at the present time, that large amounts of dialysis liquid as well as a bulky and complex apparatus are employed.

According to the present invention there is provided a process for the purification of a solution of sodium chloride containing considerable waste matter originating from blood and which has passed through a membrane, said process comprising subjecting said sodium chloride solution and waste material to electrolysis to form sodium hypochlorite and allowing said sodium hypochlorite to oxidise and destroy said waste matter.

With such a process it is possible to reduce the total volume of the liquid used during a haemodialysis session to less than about ten liters.

To facilitate the description of the present invention, reference will be made in the remainder of the text to the example of the purification and regeneration of a blood dialysis liquid.

It is known that, under the effect of a quantity of electricity of 2 Faradays ($2 \times 96,490$ coulombs), one molecule of sodium chloride combines with one molecule of water to yield one molecule of sodium hypochlorite and two atoms of hydrogen which are evolved as gas.

Electrolysis of the dialysis liquid thus forms sodium hypochlorite in situ and does so without changing the ionic strength.

It has been found that sodium hypochlorite destroys, by oxidation, the main waste matter which originated from blood and has passed into the dialysis liquid, especially nitrogen-containing waste matter, such as urea, creatinine and uric acid.

It is true that this nitrogen-containing waste matter can be adsorbed onto active charcoal, but the amounts of urea to be removed are much too high for the use of active charcoal alone to be possible in practice. It is thus necessary to add an additional system, even a non-selective system, to destroy the urea.

The manufacture in situ of sodium hypochlorite by electrolysis of the dialysis liquid has various advantages. In the first place, the concentration of chlorine-containing ions in the dialysis liquid remains constant during the entire duration of the treatment. The dialysis liquid thus remains permanently isotonic with the blood plasma and this obviously constitutes an essential advantage.

In the second place, no toxic, or even simply inconvenient, by-product is manufactured. Hydrogen, nitrogen and carbon dioxide can either be evolved directly as gases or can be dissolved in the blood and be removed by the lungs.

In addition, it is found that the volume of the dialysis liquid remains substantially constant. In effect, the consumption of 18 g of water in order to destroy 60 g of urea is negligible, having regard to the concentration of urea in the blood dialysis liquid. Furthermore, it is not necessary to add other components to the bath, with the exception, optionally, of very small amounts of a biocompatible reducing agent such as ascorbic acid. As a result, the volume of the dialysis liquid can be reduced to the amount necessary to start up the apparatus. In general, a few liters, for example 2 liters, are sufficient.

According to a second aspect of the invention, we provide apparatus comprising a haemodialyser; a first and second chamber in said haemodialyser, a membrane separating said first and second chamber, means for producing a pressure differential between said first and second chamber, an inlet and an outlet for said second chamber, a purification closed loop connected to said inlet and outlet and including means to circulate a solution of sodium chloride around said loop, an electrolyser and means to supply a direct current to said electrolyser.

The present invention will be better understood from the following description, given merely by way of example, reference being made to the accompanying drawing, in which the sole FIGURE shows schematically and without a definite scale, a particular embodiment of the apparatus according to the invention.

The apparatus illustrated includes a haemodialyser 1 provided with a dialysis membrane 2 which separates a first chamber 3, intended for the flow of the blood to be purified, from a second chamber 4 through which passes a dialysis liquid in the form of a solution of sodium chloride, for example in counter-current.

The dialysis liquid is caused to flow in a closed circuit 5 by a circulating pump 6, the pumping rate of which is not critical. A valve 15 makes it possible to control the pressure reduction in the compartment 4.

At the outlet of the haemodialyser, the dialysis liquid passes through a cartridge 7 filled with active charcoal which absorbs a portion of the waste matter which has been dialysed. The dialysis liquid then passes through an electrolysis cell 9, supplied with direct current by a generator 8. It then enters into a reactor 11, the capacity of which ensures a dwell time which makes it possible for the sodium hypochlorite produced in the electrolysis cell to destroy a sufficient amount of the urea. The reactor 11 is followed by a separator 14, equipped with a tube 13 for the removal of gases and of a volume of liquid equivalent to that which passed through the dialysis membrane by ultrafiltration. Within the reactor 11 is a heating and controlling device 12 to keep the dialysis liquid at the desired temperature, of the order of 37° to 38°C.

At the outlet of the separator, the dialysis liquid passes through a device 10 for measuring the residual hypochlorite. This device can consist of a cell for making potentiometric measurements, comprising an indicating electrode of platinum and a reference electrode of silver/silver chloride/sodium chloride, isotonic with the dialysis liquid.

A system comprising a reservoir 16 and a metering pump 17 for injecting a biocompatible reducing agent, such as ascorbic acid, into the dialysis liquid, can advantageously be added. This reducing agent destroys any traces of sodium hypochlorite which might not have reacted, at the inlet to the haemodialyser.

The electrolysis cell is closed but its shape is not critical. The electrodes are advantageously close to one another to reduce losses by the Joule effect, and can be of identical shapes. Advantageously, one of the electrodes, for example the cathode, can form the outer jacket of the cell.

As materials, it is possible to use, for the anode, materials which are resistant to oxygen, chlorine and hypochlorite in a chloride medium, such as platinum, metals or alloys covered with platinum, graphite and vitreous carbon. For the cathode, it is possible to use materials which are suitable for the electrolytic decomposition of water and for which the overvoltage for the evolution of hydrogen is lowest. For example, it is possible to use platinum, platinized metals or alloys, palladium, graphite or stainless steels.

The surface area of the cathode is not critical. The surface area of the anode is determined as a function of the current density to be employed to manufacture the desired amounts of sodium hypochlorite. This current density is generally between 1 A/dm$^2$ and 500 A/dm$^2$, and preferably between 5 and 50 A/dm$^2$. The surface area of the anode is generally between 0.6 and 6 dm$^2$. An anode with a surface area of 1 dm$^2$ is very suitable.

The electrolysis cell is supplied by a direct current generator of any known type. The characteristics of the direct current are not critical. The power of the generator is usually between 50 and 1,000 watts, but these limits are not critical.

The electric current delivered by the generator can advantageously be controlled by the cell 10 in order to maintain a substantially zero proportion of residual hypochlorite in the dialysis liquid. This corresponds to sodium hypochlorite being produced in amounts which are necessary and sufficient to destroy the urea.

The electrolysis cell can advantageously be used for producing sodium hypochlorite between two haemodialysis sessions. It is then possible to use this hypochlorite for sterilising haemodialyser circuits and/or for regenerating adsorbent products (for example, active charcoal).

The following Examples will provide a better illustration of the invention.

EXAMPLE 1

The apparatus is used which is as represented in the FIGURE and which the haemodialyser is simulated by a urea injection device. The volume of the "dialysis liquid" circuit is 5 liters and the circulating pump discharges 15 liters/hour. The electrolyser comprises a tank consisting of a stainless steel tube of internal and external diameters 4 and 6 mm, and of length 250 mm., forming the cathode and equipped with side orifices at its ends. The anode consists of a coaxial wire, made of platinum, of diameter 1.2 mm., mounted on insulating plugs. The electrodes are connected to a direct current generator with an adjustable and stabilised potential.

The original composition of the solution, which is isotonic with plasma, is as follows, in g./liter:

| | | |
|---|---|---|
| NaCl | : | 5.85 |
| NaHCO$_3$ | : | 2.7 |
| KCl | : | 0.3 |
| CaCl$_2$.2H$_2$O | : | 0.37 |
| MgCl$_2$.6H$_2$O | : | 0.15 |
| Na$_3$PO$_4$.12H$_2$O | : | 0.38 |
| Na$_2$SO$_4$.10H$_2$O | : | 0.06. |

The solution is brought to a temperature of 37°C. and to a pH of 7.4 by bubbling in CO$_2$. 1.5 g. of urea are introduced all at once, and this leads to an initial urea concentration of 0.300 g./liter. A potential difference is applied to the electrodes and a constant current of 3 A is passed for 73 minutes, which corresponds to a total amount of electricity of 14,000 coulombs.

Electrolysis is stopped and the urea is measured by the usual means, after having destroyed the traces of residual sodium hypochlorite. It is found that the final urea concentration is equal to 0.082 g./liter (27% of the initial concentration).

EXAMPLE 2

The same apparatus is used as in Example 1, but with a different electrolyser, the tube of which has internal and external diameters of 8 and 10 mm. respectively. The other conditions of the experiment are identical to those of Example 1, with the exception of the amount of urea which is introduced all at once, namely 5 g. of urea, leading to an initial urea concentration in the dialysis liquid of 1 g./liter. The final concentration is 0.76 g./liter (namely 76% of the initial concentration); it is thus found that the overall electrolysis yield increases with the average urea concentration in the "dialysis liquid."

EXAMPLES 3 to 5

The same apparatus and the same experimental conditions are used as in Example 1. Three experiments are carried out by introducing urea, all at once, and by changing the current intensity provided by the generator for each experiment. The results are shown in the following Table:

| Example | Weight of urea introduced, g. | Current intensity A | Potential V | Duration of the experiment | Weight of urea destroyed, g. |
|---|---|---|---|---|---|
| 3 | 1.54 | 4 | 11 | 1 hr. 6 mins. | 1.15 |
| 4 | 1.58 | 2 | 7.5 | 2 hrs. | 1.10 |
| 5 | 1.34 | 1 | 6.5 | 4 hrs. | 1.02 |

It is found that the weight of urea destroyed is a function of the amount of electricity used and depends only very slightly on the current densities.

EXAMPLE 6

The same apparatus and the same experimental conditions are used as in Example 2. However, 5.12 g. of urea are introduced initially, and then 77 ccs. of an aqueous solution of urea containing 50 g./liter of urea, that is to say 3.85 g. of additional urea, are introduced continuously during the experiment. The experiment lasts for 5 hours 11 minutes. The residual urea at the end of the experiment is measured; it is found that 4.55 g. of urea (50.7% of the urea introduced) have been destroyed.

EXAMPLE 7

The same apparatus and the same experimental conditions are used as in Example 2. 5.25g. of creatinine are introduced all at once, to give an initial creatinine concentration of 1.05 g./liter in the "dialysis liquid." A potential is applied to the electrodes and a constant current of 3 A is passed for 4 hours, which corresponds to a total amount of electricity of 43,200 coulombs.

Electrolysis is stopped and the residual creatinine is measured. It is found that the final creatinine concentration is 0.1 g./liter.

EXAMPLE 8

The same apparatus and the same experimental conditions are used as in Example 2. 2.5 g. of uric acid are introduced all at once, to give an initial uric acid concentration in the "dialysis liquid" of 0.5 g./liter. A constant current of 3 A is applied, corresponding to a potential difference of 10 volts. It is found that the residual uric acid concentrations are as follows: After 15 minutes, (2,700 coulombs), concentration: 0.331g./l. After 30 minutes, (5,400 coulombs), concentration: 0.200g./l. After 45 minutes, (8,100 coulombs), concentration: 0.025 g./l.

It is found that the uric acid disappears in a substantially linear manner.

EXAMPLE 9

A circuit of the type represented in the FIGURE is used, comprising only and successively a haemodialyser 1, a circulating pump 6, an electrolyser 9, a reactor 11 and a container of active charcoal 7.

The haemodialyser is of the type described in French Pat. No. 1,597,874; the membrane surface area reaches 1 m².

The electrolyser consists of 8 cells in parallel. Each cell comprises a cathode consisting of a cylindrical stainless steel tube of diameters 8 and 10 mm. and of length 250 mm., open at its ends, and an anode consisting of a platinum wire of diameter 1 mm., attached coaxially to the tube through two insulating plugs. The total surface area of the anode is approximately 0.6 dm². The electrodes are connected to a direct current generator, with an adjustable and stabilised potential.

The charcoal cartridge is filled with 170 g. of active charcoal of the type CECA - NC 45, which has first been washed with water.

Blood circuit — The patient is simulated by 35 liters of a solution which is isotonic with plasma, the composition of which is given in Example 1. The following are added before the experiment: (35 g. of glucose, namely 1 g./liter, (67.5 g. of urea, namely 1.93 g./liter, (7.35 g. of creatinine, namely 0.21 g./liter and (3.64 g. of uric acid, namely 0.104 g./liter).

This liquid is made to flow through the compartment 3 of the haemodialyser at the rate of 200 ccs./minute.

Dialysis solution circuit — The above solution is purified by dialysis against 10 liters of an isotonic solution, the composition of which is given in Example 1 and to which 10 g. of glucose (namely 1 g./liter) only have been added. The pH of this solution is brought to 7.4 by bubbling in CO₂. The temperatures of the solutions are kept at 37° – 38°C. The dialysis solution is circulated at a rate of 500 ccs./minute. A pressure difference of 200 mm. of mercury is maintained between the chambers 3 and 4 of the haemodialyser, 15 Minutes after the start of the dialysis, a potential is applied to the electrodes. In all, 40 amperes are passed through the 8 cells for 5 hours, that is to say 720,000 coulombs.

At the end of the experiment, the urea, creatinine and uric acid in the "blood circuit" are measured. The following results are obtained:

|  | Weight removed | % removed |
|---|---|---|
| urea | 34.6 g | 51.3 |
| creatinine | 3.4 g. | 47.5 |
| uric acid | 2.26 g. | 61.5 |

In addition, the following observations are made:
a. No hypochlorite ion is detected, either in the circuit simulating blood, or in the dialysis solution at the inlet to the haemodialyser.
b. The volume of ultrafiltered liquid is 1.6 liters.
c. The final pH of the dialysis solution is 7.2.
d. The final solutions do not show any acute toxicity when administered intravenously to mice.

EXAMPLE 10

The experiment consists of dialysing sheep's blood overloaded with waste matter, of measuring the degrees of purification by a solution regenerated by electrolysis and of checking the general behaviour of the blood of the animal.

An apparatus similar to that described in Example 9 is used.

The chamber 3 of the haemodialyser is supplied with 200 ml./minute of arterial blood removed from a sheep which had previously been equipped with an arterial-venous shunt. The purified blood is returned into the vein.

Before introducing the blood into the haemodialyser, 4 ml/minute of a sterile aqueous solution of sodium chloride (9/g/l), of urea (30 g/l) and of creatinine (3 g/l) are added.

A solution, which flows in a closed circuit at a rate of 200 ml/minute, passes through the compartment 4 of the haemodialyser, the initial volume of this solution being 9 liters and its composition being as follows:

| | |
|---|---|
| NaCl | 6.1 g/l |
| NaHCO₃ | 5.14 g/l |
| KCl | 0.34 g/l |
| MgCl₂.6H₂O | 0.19 g/l |
| CaCl₂.2H₂O | 0.42 g/l |

The pH is brought to a value of 7.4 by bubbling in CO₂.

This solution is isotonic with sheep plasma.
The temperature of the solution is kept at 38.5°C.
The dialysis lasts for 4 hours 10 minutes.
The solution is electrolyzed for 4 hours with a current intensity of 40 amperes.
The necessary electrolysis potential is 9.5 volts.
During the entire experiment, the urea and the creatinine are measured by the usual means, by removing samples simultaneously from the blood and from the dialysis solution, respectively at the inlet and outlet of the haemodialyser.

During the dialysis, 14.5 g of urea on the one hand and 1.3 g of creatinine on the other hand, are thus removed from the blood.

The dialysis solution contains less than 10 mg/l of urea, 1 mg/l of creatinine and 10 mg/l of hypochlorite ion.

The working conditions, particularly the relative speeds of the fluids in the haemodialyser and the concentrations of the waste matter in the blood (1 g/l of urea and 0.1 g/l of creatinine), give average clearances of 62% for the two waste materials.

The volume of ultrafiltrate reaches 1.1 liters.

Furthermore, by measuring the plasma iron, a complete absence of haemolysis of the sheep's blood is observed. The concentration of iron in the blood plasma remains at an average value of 2.5 mg/l.

All the other parameters checked in the blood (pressure of $CO_2$, pressure of $O_2$, pH and ionic strength) remain in a satisfactory range.

The present invention can be the subject of diverse variants within the scope of the technician. Thus, without implying a limitation, the electrolyser 9 can consist of several electrolysis cells arranged in series and/or in parallel; the various apparatuses can be placed in the closed circuit 5 in a different order. It is possible to substitute other systems for the active charcoal, such as selective absorbents or ion exchange resins. The electrolyser can be placed in a dialysis liquid circuit which is partially used in open circuit. The electrolyser can be placed in a compartment which collects a blood ultrafiltrate.

In general terms, the process described in the particular case of regenerating a dialysis liquid can be used for purifying any solution of sodium chloride containing oxidisable waste matter originating from blood. For example, it can be suitable for treating hospital waste water.

What is claimed is:

1. Apparatus for the purification of blood, said apparatus comprising a haemodialyzer, a first and second chamber in said haemodialyzer, a membrane separating said first and second chamber, means for producing a pressure differential between said first and second chamber, an inlet and an outlet for said second chamber, a purification closed loop connected to said inlet and outlet said loop including (i) means to circulate a solution of sodium chloride around said loop, (ii) an electrolyzer and, (iii) a separator permitting the removal from the closed loop of gases and of a volume of liquid and means to supply a direct current to said electrolyzer.

2. Apparatus as claimed in claim 1 and further comprising a device for measuring the residual concentration of sodium hypochlorite in the closed loop at the inlet to the second chamber, said device being operatively connected to said direct current supply means to control the supply of current effective to reduce said concentration to a minimum.

* * * * *